US011034985B2

(12) United States Patent
Ochrombel et al.

(10) Patent No.: US 11,034,985 B2
(45) Date of Patent: Jun. 15, 2021

(54) METHOD FOR PRODUCING L-METHIONINE

(71) Applicant: EVONIK OPERATIONS GMBH, Essen (DE)

(72) Inventors: Ines Ochrombel, Bielefeld (DE); Daniel Fischer, Midlothian, VA (US); Brigitte Bathe, Salzkotten (DE); Marleen Hasselmeyer, Paderborn (DE); Michael Hampel, Velsdorf (DE); Joanne Pedall, Melle (DE)

(73) Assignee: EVONIK OPERATIONS GMBH, Essen (DE)

( * ) Notice: Subject to any disclaimer, the term of this patent is extended or adjusted under 35 U.S.C. 154(b) by 0 days.

(21) Appl. No.: 15/778,762

(22) PCT Filed: Nov. 1, 2016

(86) PCT No.: PCT/EP2016/076281
§ 371 (c)(1),
(2) Date: May 24, 2018

(87) PCT Pub. No.: WO2017/089077
PCT Pub. Date: Jun. 1, 2017

(65) Prior Publication Data
US 2018/0346946 A1    Dec. 6, 2018

(30) Foreign Application Priority Data
Nov. 27, 2015  (EP) .................... 15196776

(51) Int. Cl.
C12P 13/12    (2006.01)

(52) U.S. Cl.
CPC ....... *C12P 13/12* (2013.01); *C12Y 203/01031* (2013.01); *C12Y 205/01049* (2013.01)

(58) Field of Classification Search
None
See application file for complete search history.

(56) References Cited

U.S. PATENT DOCUMENTS

| | | | |
|---|---|---|---|
| 3,598,701 A | 8/1971 | Tanaka et al. | |
| 6,090,597 A | 7/2000 | Hirano et al. | |
| 6,221,636 B1 | 4/2001 | Hayakawa et al. | |
| 6,303,348 B1 | 10/2001 | Livshits et al. | |
| 6,812,016 B2 * | 11/2004 | Moeckel | C12N 9/88 435/106 |
| 7,332,310 B2 * | 2/2008 | Nakagawa | C07K 14/34 435/115 |
| 7,611,873 B1 | 11/2009 | Usuda et al. | |
| 7,785,779 B2 | 8/2010 | Kroger et al. | |
| 7,790,424 B2 | 9/2010 | Park et al. | |
| 7,884,240 B2 * | 2/2011 | Hateley | C07C 319/14 562/559 |
| 8,044,191 B2 | 10/2011 | Kroger et al. | |
| 8,252,579 B2 | 8/2012 | Meynial-Salles et al. | |
| 8,551,742 B2 | 10/2013 | Brazeau et al. | |
| 8,735,159 B2 | 5/2014 | Zelder et al. | |
| 8,795,990 B2 | 8/2014 | Bestel-Corre et al. | |
| 9,034,611 B2 | 5/2015 | Dischert et al. | |
| 9,062,332 B2 | 6/2015 | Schneider et al. | |
| 9,562,245 B2 | 2/2017 | Schneider et al. | |
| 9,732,364 B2 | 8/2017 | Figge et al. | |
| 9,988,655 B2 | 6/2018 | Figge et al. | |
| 10,196,658 B2 | 2/2019 | Dischert et al. | |
| 10,329,591 B2 | 6/2019 | Figge et al. | |
| 2009/0253186 A1 | 10/2009 | Kim et al. | |
| 2016/0177352 A1 | 6/2016 | Dischert et al. | |
| 2017/0051323 A1 | 2/2017 | Ochrombel et al. | |
| 2017/0051324 A1 | 2/2017 | Ochrombel et al. | |
| 2017/0240938 A1 | 8/2017 | Figge et al. | |
| 2017/0306366 A1 | 10/2017 | Figge et al. | |
| 2018/0223319 A1 | 8/2018 | Soucaille et al. | |
| 2019/0085340 A1 | 3/2019 | Thierbach et al. | |
| 2019/0185890 A1 | 6/2019 | Voss et al. | |

FOREIGN PATENT DOCUMENTS

| | | |
|---|---|---|
| EP | 1 149 911 | 10/2001 |
| EP | 2 290 051 A1 | 3/2011 |
| EP | 2 292 783 | 3/2011 |
| EP | 2 657 250 | 10/2013 |
| EP | 2 657 345 | 10/2013 |
| JP | 2000/157267 | 6/2000 |
| WO | WO 93/17112 | 9/1993 |
| WO | WO 95/25785 | 9/1995 |
| WO | WO 02/10209 A1 | 2/2002 |
| WO | WO 02/18613 | 3/2002 |
| WO | WO 2004/067757 | 8/2004 |
| WO | WO 2005/111202 A1 | 11/2005 |
| WO | WO 2007/011939 | 1/2007 |

(Continued)

OTHER PUBLICATIONS

Ferla et al. (Microbiology, 2014, vol. 160, pp. 1571-1584).*
Kase et al. (Agricul. & Biol. Chem., vol. 39, Issue 1, 1975, pp. 153-160).*
International Search Report for corresponding international application PCT/EP2016/076281 filed Nov. 1, 2016.
Written Opinion of the International Searching Authority for corresponding international application PCT/ EP2016/076281 filed Nov. 1, 2016.
International Preliminary Report on Patentability for corresponding international application PCT/EP2016/076281 filed Nov. 1, 2016.
Armstrong, "The Preparation of $_D$- and $_L$-Homoserine," *J. Am. Chem. Soc.* 70(5):1756-1759 (May 1948).

(Continued)

*Primary Examiner* — Hope A Robinson
(74) *Attorney, Agent, or Firm* — Law Office of: Michael A. Sanzo, LLC

(57) ABSTRACT

The present invention relates to a method for producing L-methionine in which a microorganism is cultured in the presence of L-homoserine and methyl mercaptan, a salt of the same or dimethyl disulfide whereby the L-methionine is accumulated in the culture medium.

16 Claims, 2 Drawing Sheets
Specification includes a Sequence Listing.

(56) References Cited

FOREIGN PATENT DOCUMENTS

| WO | WO 2007/024933 | | 3/2007 |
|---|---|---|---|
| WO | WO 2007/077041 | A1 | 7/2007 |
| WO | WO 2008/013432 | | 1/2008 |
| WO | WO 2008/116852 | A1 | 10/2008 |
| WO | WO 2008/127240 | A1 | 10/2008 |
| WO | WO 2009/043803 | A2 | 4/2009 |
| WO | WO 2010/020681 | A1 | 2/2010 |
| WO | WO 2011/073122 | A1 | 6/2011 |
| WO | WO 2011/073738 | A1 | 6/2011 |
| WO | WO 2011/080301 | A2 | 7/2011 |
| WO | WO 2011/080542 | A2 | 7/2011 |
| WO | WO 2012/055798 | A1 | 5/2012 |
| WO | WO 2013/001055 | A1 | 1/2013 |
| WO | WO 2013/190343 | A1 | 12/2013 |
| WO | WO 2015/028674 | A1 | 3/2015 |
| WO | WO 2015/028675 | | 3/2015 |

OTHER PUBLICATIONS

Bolton, et al., "Towards Methionine Overproduction in *Corynebacterium glutamicum*—Methanethiol and Dimethylsulfide as Reduced Sulfur Sources," *J. Microbiol. Biotechnol.* 20(8):1196-1203 (Aug. 2010).

Booth, et al., "Regulation of Cytoplasmic pH in Bacteria," *Microbiological Reviews* 49(4):359-378 (Dec. 1985).

De Boer, et al., "The tac promoter: A functional hybrid derived from the trp and lac promoters," *Proc. Natl. Acad. Sci. USA* 80(1):21-25 (Jan. 1983).

Eikmanns, et al., "A family of *Corynebacterium glutamicum/Escherichia coli* shuttle vectors for cloning, controlled gene expression, and promoter probing," *Gene* 102(1):93-98 (Jun. 1991).

Figge, "Methionine Biosynthesis in *Escherichia coli* and *Corynebacterium glutamicum*," *Microbiol Monogr* (5):163-193, Springer-Verlag Berlin Heidelberg ((2007).

Gerstmeir, et al., "Acetate metabolism and its regulation in *Corynebacterium glutamicum*," *Journal of Biotechnology* 104(1-3):99-122 (Sep. 2003).

Kosuge, et al., "Analysis of the Methionine Biosynthetic Pathway in the Extremely Thermophilic Eubacterium *Thermus thermophilus*," *Journal of Bioscience and Bioengineering* 90(3):271-279 (Jan. 2000).

Kumari, et al., "Cloning, Characterization, and Functional Expression of acs, the Gene Which Encodes Acetyl Coenzyme a Synthetase in *Escherichia coli*," *Journal of Bacteriology* 177(10):2878-2886 (May 1995).

Lisser, et al., "Compilation of *E. coli* mRNA promoter sequences," *Nucleic Acids Research* 21(7):1507-1516 (Apr. 1993).

Liu, et al., "YjeH Is a Novel Exporter of $_L$-Methionine and Branched-Chain Amino Acids in *Escherichia coli*," *Applied and Environmental Microbiology* 81(22):7753-7766 (Nov. 2015).

Pátek, et al., "Promoters from *Corynebacterium glutamicum*: cloning, molecular analysis and search for a consensus motif," *Microbiology* 142(5):1297-1309 (May 1996).

Pátek, et al., "Corynebacterium glutamicum promoters: a practical approach," *Microbial Biotechnology* 6(2):103-117 (Mar. 2013).

Pátek, et al., "Promoters and Plasmid Vectors of *Corynebacterium glutamicum*," *Microbiol Monogr* (23):51-88, Springer-Verlag Berlin Heidelberg ((2013).

Tauch, et al., "Isoleucine uptake in *Corynebacterium glutamicum* ATCC 13032 is directed by the brnQ gene product," *Arch. Microbiol.* 169(4):303-312 (Apr. 1998).

Teas, et al., "Homoserine as a Precursor of Threonine and Methionine in Neurospora," *J. Biol. Chem.* 172(2):651-658 (Feb. 1948).

Templeton, et al., "Transport of Biosynthetic Intermediates: Homoserine and Threonine Uptake in *Escherichia coli*," *Journal of Bacteriology* 117(3):1002-1009 (Mar. 1974).

Trötschel, et al., "Characterization of Methionine Export in *Corynebacterium glutamicum*," *Journal of Bacteriology* 187(11):3786-3794 (Jun. 2005).

Yamagata, et al., "Partial Purification and Some Properties of Homoserine O-Acetyltransferase of a Methionine Auxotroph of *Saccharomyces cerevisiae*," *Journal of Bacteriology* 169(8):3458-3463 (Aug. 1987).

Guo, et al., "Protein tolerance to random amino acid change," *PNAS USA* 101(25):9205-9210 (Jun. 22, 2004).

Yamada, et al., "$_L$-Methionine Overproduction by Ethionine-resistant Mutants of Obligate Methylotroph Strain OM 33," *Agric. Biol. Chem.* 46(1):47-55 (1982).

European Search Report and machine translation of European Search Opinion for corresponding EP 15 19 6776.

International Search Report for PCT/IB2015/001888 dated Aug. 7, 2015, corresponding to copending U.S. Appl. No. 15/750,516.

Written Opinion of the International Searching Authority for PCT/IB2015/001888 dated Aug. 7, 2015, corresponding to copending U.S. Appl. No. 15/750,516.

International Preliminary Report on Patentability for PCT/IB2015/001888 dated Aug. 7, 2015, corresponding to copending U.S. Appl. No. 15/750,516.

Agren, et al., "Cysteine Synthase (CysM) of *Mycobacterium tuberculosis* Is an O-Phosphoserine Sulfhydrylase," *Journal of Biological Chemistry* 283(46):31567-31574 (Nov. 2008).

Bourhy, et al., "Homoserine O-Acetyltransferase, Involved in the *Leptospira meyeri* Methionine Biosynthetic Pathway, Is Not Feedback Inhibited," *Journal of Bacteriology* 179(13):4396-4398 (Jul. 1997).

Carrier, et al., "Library of Synthetic 5' Secondary Structures to Manipulate mRNA Stability in *Escherichia coli*," *Biotechnol. Prog.* 15(1):58-64 (Sep. 1999).

Krishnamoorthy, et al., "Protein Thiocarboxylate-Dependent Methionine Biosynthesis in *Wolinella succinogenes*," *JACS* 133(2):379-386 (Jan. 2011).

Lee, et al., "Methionine biosynthesis and its regulation in *Corynebacterium glutamicum*: parallel pathways of transsulfuration and direct sulfhydrylation," *Appl. Microbiol. Biotechnol.* 62(5-6):459-467 (Oct. 2003).

Saunderson, "Comparative metabolism of $_L$-methionine, $_{DL}$-methionine and $_{DL}$-2-hydroxy 4-methylthiobutanoic acid by broiler chicks," *British Journal of Nutrition* 54(3):621-633 (Nov. 1985).

Taylor, et al., "Thiamin Biosynthesis in *Escherichia coli*," *Journal of Biological Chemistry* 273(26):16555-16560 (Jun. 1998).

Tran, et al., "A novel mechanism of sulfur transfer catalyzed by O-acetylhomoserine sulfhydrylase in the methionine biosynthetic pathway of *Wolinella succinogenes*," *Acta Crystallographica Section D: Biological Crystallography* 71(16):831-838 (Sep. 2011).

U.S. Appl. No. 14/915,137, filed Feb. 26, 2016, US-2016/0177352 A1, Jun. 23, 2016, Dischert.

U.S. Appl. No. 15/507,435, filed Feb. 28, 2017, US-2017/0240938 A1, Aug. 24, 2017, Figge.

U.S. Appl. No. 15/646,940, filed Jul. 11, 2017, US-2017/0306366 A1, Oct. 26, 2017, Figge.

U.S. Appl. No. 15/750,516, filed Feb. 6, 2018, US-2018/0223319 A1, Aug. 9, 2018, Soucaille.

Restriction Requirement dated Jun. 13, 2019 for copending U.S. Appl. No. 15/570,516.

Response to Restriction Requirement dated Aug. 13, 2020 for copending U.S. Appl. No. 15/570,516.

Office Action dated Oct. 23, 2019 for copending U.S. Appl. No. 15/570,516.

Amendment & Response to Office Action dated Jan. 23, 2020 for copending U.S. Appl. No. 15/570,516.

Final Office Action dated Mar. 6, 2020 for copending U.S. Appl. No. 15/570,516.

Amendment & Response to Final Office Action dated Jul. 20, 2020 for copending U.S. Appl. No. 15/570,516.

Request for Continued Examination for copending U.S. Appl. No. 15/570,516.

* cited by examiner

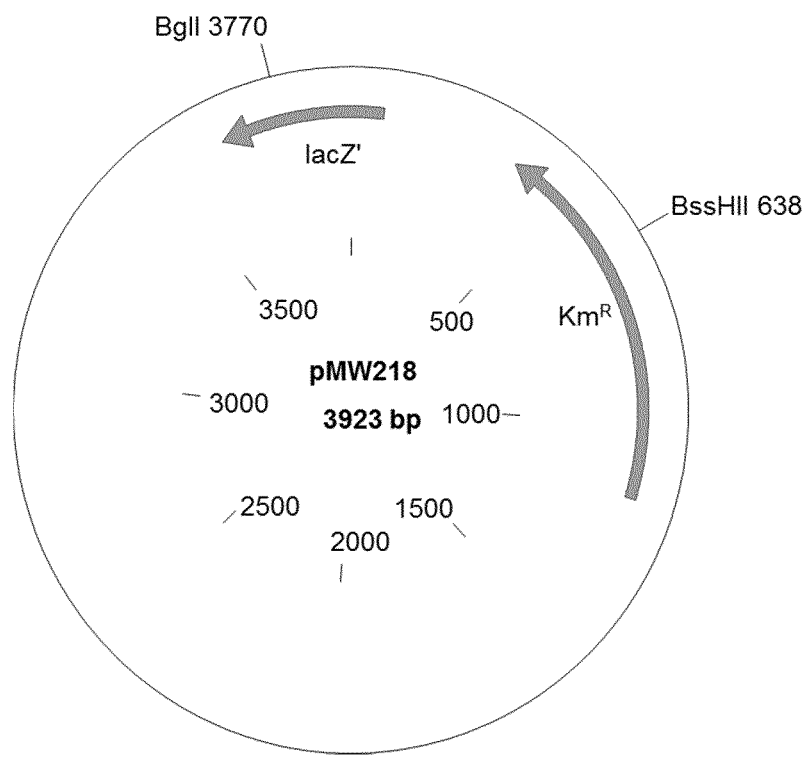
Figure 1: pMW218 plasmid map
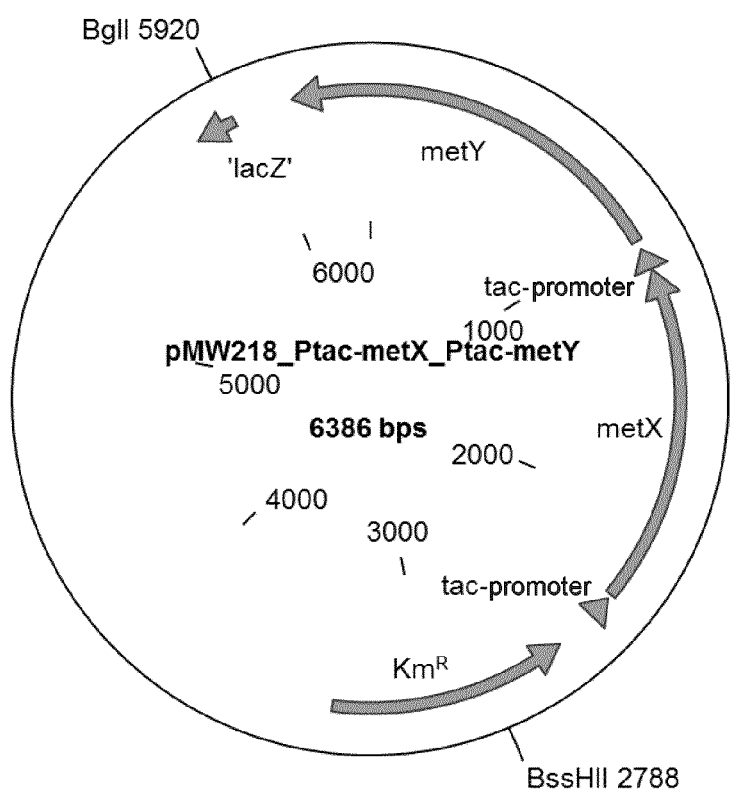
Figure 2: pMW218_Ptac-metX_Ptac-metY plasmid map

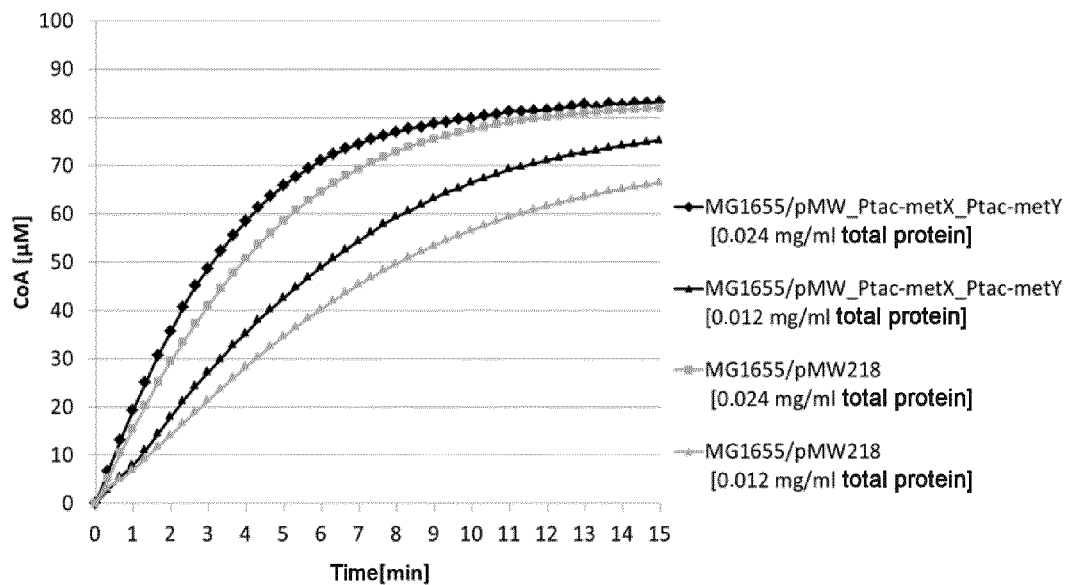

Figure 3: Catalytic conversion of L-homoserine and acetyl-CoA by the cell homogenates of MG1655/pMW218 or MG1655/pMW218_Ptac-metX_Ptac-metY.

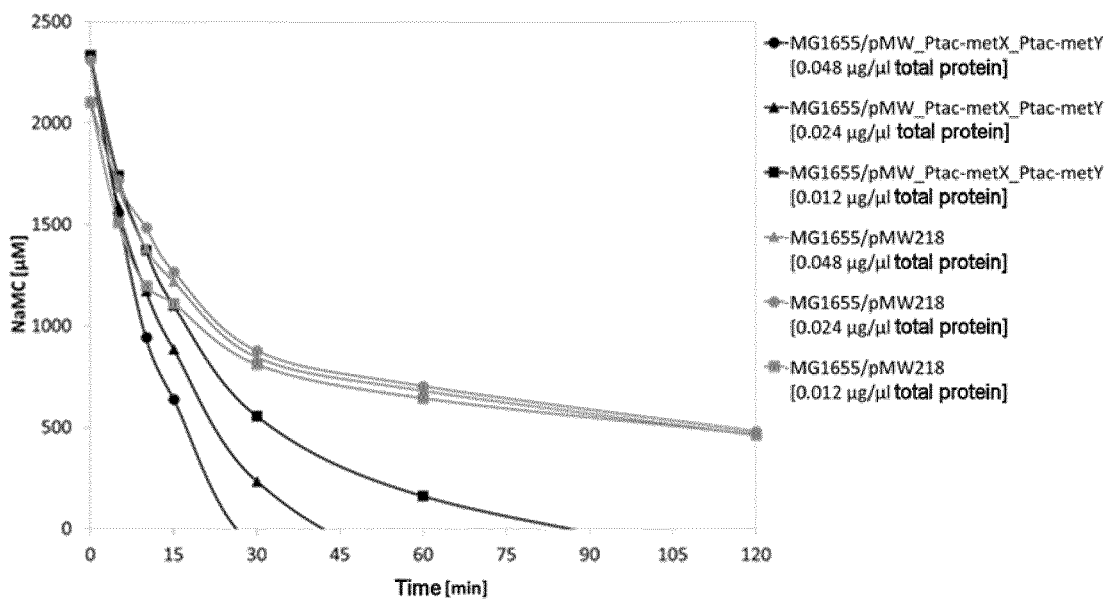

Figure 4: Catalytic conversion of sodium methyl mercaptide in the presence of O-acetylhomoserine and pyridoxal 5'-phosphate (PLP) by the O-acetylhomoserine sulfhydrylase enzyme (MetY). Comparison of the cell homogenates of MG1655/pMW218 and MG1655/pMW218_Ptac-metX_Ptac-metY is shown with the respective total protein concentrations used.

METHOD FOR PRODUCING L-METHIONINE

CROSS REFERENCE TO RELATED APPLICATIONS

The present application is US national stage of international application PCT/EP2016/076281, which had an international filing date of Nov. 1, 2016, and which was published on Jun. 1, 2017. Priority is claimed to European application EP 15196776.7, filed on Nov. 27, 2015.

SEQUENCE LISTING

The instant application contains a Sequence Listing which has been submitted in ASCII format via EFS-Web. The Sequence Listing was created on, Jun. 28, 2018 is named Ochrombel-1.txt and is 24,576 bytes in size. This Sequence Listing is hereby incorporated by reference in its entirety.

The present invention relates to a method for producing L-methionine in which a microorganism is cultured in the presence of L-homoserine and methyl mercaptan, a salt of the same or dimethyl disulfide whereby the L-methionine is accumulated in the culture medium.

The amino acid methionine is currently industrially produced worldwide in large amounts and is of considerable commercial importance. Methionine is employed in many fields, such as pharmaceutical, health and fitness products, but particularly as feedstuff additive in many feedstuffs for various livestock, where both the racemic and the enantiomerically pure form of methionine may be used.

On an industrial scale, methionine is produced chemically via the Bucherer-Bergs reaction, which is a variant of the Strecker synthesis. In this case, the starting substances methylmercaptopropionaldehyde (prepared from acrolein and methyl mercaptan), hydrogen cyanide, ammonia and carbon dioxide are reacted to give 5-(2-methylmercaptoethyl) hydantoin (methionine hydantoin), this subsequently being hydrolysed by alkali to give the alkali metal methioninate and the methionine then being liberated by neutralisation with acid (EP 0 780 370 A2). Various other methods can also be used to prepare methionine, for example, the amidocarbonylation reaction, the hydrolysis of proteins or the fermentation of microorganisms producing-methionine. In chemical synthesis, methionine is produced as a racemic mixture of D- and L-methionine, whereas L-methionine, or L-configured precursors of the same, L-homoserine for example, can be produced by the fermentation of suitable microorganisms.

L-Homoserine, a potential precursor of L-methionine (H. J. Teas et al., J. Biol. Chem. 1948, 172: 651-658), can be produced both chemically (M. D. Armstrong, J. Am. Chem. Soc., Vol. 70, 1756-1759, 1948) and by fermentation by means of microorganisms (see e.g. U.S. Pat. Nos. 3,598,701, 6,303,348 B1, EP 0 994 190 A2, EP 1 149 911 A2, WO 2004/067757 A1).

Hateley et al. disclose a method in which L-methionine is obtained by a chemical route starting from L-homoserine (WO 2007/085514 A2).

Lievense was able to prove that microorganism strains lacking homocysteine methylase activity, whose L-homoserine production had been upregulated and which had been transformed with a plasmid encoding an L-homoserine acetyltransferase and an O-acetyl-L-homoserine sulfhydrylase (O-acetylhomoserine (thiol)-lyase), produced L-methionine in excess of their own need in the presence of methyl mercaptan, in contrast to the original strain (*E. coli, C. glutamicum* or *B. flavum*) (WO 93/17112 A1).

Bolten et al. (J. Microbiol. Biotechnol. (2010), 20(8), 1196-1203) could show that (wildtype) *C. glutamicum* is able to grow on methyl mercaptan and on its dimeric form, dimethyl disulfide, as sole sulphur sources instead of sulfate, the most common sulphur source for the cultivation of microorganisms, and investigated the underlying pathways and enzymes. They demonstrated that MetY (O-acetyl-L-homoserine sulfhydrylase) is responsible for the substitution of the acetyl group of O-acetyl-L-homoserine by the mercapto group of methylmercaptan or of dimethyl disulfide to directly yield L-methionine. In order to increase L-methionine production the authors suggest the amplification not only of the MetY, but also of other enzymes of the L-methionine biosynthesis.

Zelder et al. (WO 2007/011939 A2) demonstrated, that L-methionine can be produced in microorganisms, such as *E. coli* and *C. glutamicum*, by culturing the microorganisms having a deregulated O-acetyl-L-homoserine sulfhydrylase or O-succinyl-L-homoserine sulfhydrylase and/or L-homoserine acetyltransferase or L-homoserine succinyltransferase in the presence of a methyl capped sulfide compound, such as dimethyl disulfide or dimethyl trisulfide.

A two-stage biotechnological method for preparing L-methionine is proposed by Kim et al. (WO 2008/013432 A1). In a first step here, an L-methionine precursor, O-succinyl-L-homoserine or O-acetyl-L-homoserine, is initially obtained by means of recombinant microorganisms, which are accumulated in the culture broth. In the subsequent second step, the L-methionine precursor is reacted with methyl mercaptan in the presence of a protein having O-succinyl-L-homoserine sulfhydrylase activity or O-acetyl-L-homoserine sulfhydrylase activity or in the presence of a microorganism producing such protein or a cell digest of this microorganism, to give L-methionine and the corresponding carboxylic acid, i.e. acetate or succinate.

However, in this enzymatic reaction, equimolar amounts of acetate or succinate are formed in addition to L-methionine. On choosing O-acetyl-L-homoserine as L-methionine precursor, for example, this leads to high acetate concentrations in the course of the reaction, particularly on an industrial scale. At a low external pH, undissociated acetate molecules can get into the cell across the membrane and be deprotonated therein, which leads to a fall in the internal pH of the cytoplasm and which perturbs the cell pH homeostasis (I. R. Booth, Microbiological Reviews 49, No. 4 (1985), 359-378). Furthermore, acetate cannot be completely removed from the L-methionine product with acceptable effort. Accordingly, Hong et al. (WO 2012/091479 A2) propose numerous methods to remove and to reuse the relatively large amounts of acetate generated in the second stage of the L-methionine production process from the L-methionine product.

The object of the present invention is to provide a process for producing L-methionine in a microorganism in which the acetate formed in the conversion of O-acetyl-L-homoserine to L-methionine is substantially reused by the same microorganism.

This object is achieved by a method for producing L-methionine, wherein a microorganism having L-homoserine O-acetyltransferase activity and O-acetyl-L-homoserine sulfhydrylase activity is cultured in a culture medium comprising L-homoserine and a sulphur source, the sulphur source being selected from the group consisting of methyl mercaptan (MC), a methyl mercaptan salt and dimethyl disulfide (DMDS), whereby L-methionine is accumulated in the culture medium Enzyme activities in microorganisms are generally effected by the expression of the corresponding gene encoding the respective enzyme. So-called promoters are located upstream of the gene. A promoter is a DNA sequence consisting of about 40 to 50 base pairs and which constitutes the binding site for an RNA polymerase holoenzyme and the transcriptional start point (M. Pátek et al., Microbial Biotechnology, 6 (2013), 103-117), whereby the strength of expression of the controlled polynucleotide or gene can be influenced. A "functional linkage" is understood to mean the sequential arrangement of a promoter with a gene, which leads to a transcription of the gene.

The microorganism may also be recombinant and have enhanced L-homoserine O-acetyltransferase activity and enhanced O-acetyl-L-homoserine sulfhydrylase activity.

Enhanced enzyme activities in microorganisms can be effected, for example, by mutation of the corresponding endogenous gene. Enzyme activities can also be enhanced by increasing the expression of the corresponding gene, for example, by increasing the gene copy number and/or by enhancing gene regulatory factors. The enhancement of such regulatory factors which positively influence gene expression can, for example, be achieved by modifying the promoter sequence upstream of the structural gene in order to increase the effectiveness of the promoter or by completely replacing said promoter with a more effective promoter.

In the method according to the present invention, the L-homoserine O-acetyltransferase activity and the O-acetyl-L-homoserine sulfhydrylase activity are both preferably enhanced by increased expression of a gene which encodes a protein having L-homoserine O-acetyltransferase activity or a protein having O-acetyl-L-homoserine sulfhydrylase activity. The increased gene expression is preferably achieved by increasing the copy number of the gene encoding the protein having L-homoserine O-acetyltransferase activity or the protein having O-acetyl-L-homoserine sulfhydrylase activity and/or by functional linkage in each case of the gene encoding the protein having L-homoserine O-acetyltransferase activity or the protein having O-acetyl-L-homoserine sulfhydrylase activity to a strong promoter.

Suitable strong promoters or methods of producing such promoters for increasing expression are known from the literature (e.g. S. Lisser and H. Margalit, Nucleic Acid Research, 1993, Vol. 21, No. 7, 1507-1516; M. Pátek and J. Nesvera in H. Yukawa and M Inui (eds.), Corynebacterium glutamicum, Microbiology Monographs 23, Springer Verlag Berlin Heidelberg 2013, 51-88; B. J. Eikmanns et al., Gene, 102 (1991) 93-98). For instance, native promoters may be optimized by altering the promoter sequence in the direction of known consensus sequences with respect to increasing the expression of the genes functionally linked to these promoters (M. Patek et al., Microbiology (1996), 142, 1297-1309; M. Patek et al., Microbial Biotechnology 6 (2013), 103-117). To increase the expression of the gene encoding the protein having L-homoserine O-acetyltransferase activity (metX) or the gene encoding the protein having O-acetyl-L-homoserine sulfhydrylase activity (metY), the tacI promoter (PtacI), for example, is suitable (H. A. deBoer et al., Proc. Natl. Acad. Sci. USA, Vol. 80, 21-25, January 1983, Biochemistry). The sequence of PtacI is shown under sequence number 5 (SEQ ID NO:5).

Constitutive promoters are also suitable for the overexpression, in which the gene encoding the enzyme activity is expressed continuously under the control of the promoter such as, for example, the glucose dependent deo promoter. Chemically induced promoters are also suitable, such as tac, lac or trp. The most widespread system for the induction of promoters is the lac operon of E. coli. In this case, either lactose or isopropyl ß-D-thiogalactopyranoside (IPTG) is used as inducer. Also systems using arabinose (e.g. the pBAD system) or rhamnose (e.g. E. coli KRX) are common as inducers. A system for physical induction is, for example, the temperature-induced cold shock promoter system based on the E. coli cspA promoter from Takara or Lambda PL and also osmotically inducible promoters, for example, osmB (e.g. WO 95/25785 A1).

In the method according to the present invention, the recombinant microorganism is selected from the group consisting of Enterobacteriaceae and Corynebacteriaceae, for example an Escherichia coli (E. coli) strain, e.g. the non-pathogenic E. coli K-12 strain MG1655 (DSM 18039), or a Corynebacterium glutamicum (C. glutamicum) strain, e.g. ATCC13032, or a Corynebacterium humireducens (C. humireducens) strain, e.g. DSM 45392.

In the method according to the present invention, the L-homoserine O-acetyltransferase activity is, for example, the enzyme MetX, which originates from Corynebacterium glutamicum or from C. humireducens. Kim et al. (EP 2 657 345 A1; EP 2 657 250 A2) or Ochrombel et al. (WO 2015/165746 A1) disclose examples of suitable enzymes having L-homoserine O-acetyltransferase activity. The enzyme MetX used in the experimental examples described below has the amino acid sequence according to sequence number 2 (SEQ ID NO:2). The corresponding nucleotide sequence for the gene metX is shown under sequence number 1 (SEQ ID NO:1). The sequence originates from C. glutamicum (ATTC13032) NC 003450.

An O-acetyl-L-homoserine sulfhydrylase activity suitable for the method according to the present invention is, for example, the enzyme MetY, which originates from Corynebacterium glutamicum or C. humireducens. Möckel et al. (WO 02/18613 A1), Kroger et al. (WO 2007/024933 A2) or Kim et al. (EP 2 657 345 A1) disclose examples of enzymes having O-acetyl-L-homoserine sulfhydrylase activity according to the invention. The enzyme MetY used in the experimental examples described below has the amino acid sequence according to sequence number 4 (SEQ ID No. 4). The corresponding nucleotide sequence for the gene metY is shown under sequence number 3 (SEQ ID NO:3). The sequence originates from C. glutamicum (ATTC13032) NC 003450.

L-Homoserine is transported into the microorganisms via importers for branched-chain amino acids, e.g. the LIV system in Escherichia coli (B. A. Templeton and M. A. Savageau, JOURNAL OF BACTERIOLOGY, Vol. 117, No. 3, March 1974, p. 1002-1009). In Corynebacterium glutamicum (C. glutamicum) there is also an homologous transport system encoded by, BrnQ of cgl2310 (A. Tauch et al., Arch Microbiol 169 (1998): 303-312).

Within the cell, the L-homoserine is activated on its hydroxyl group by the transfer of the acetyl group of acetyl coenzyme A (acetyl-CoA) to give O-acetyl-L-homoserine via an (heterologous) homoserine O-acetyltransferase (MetX). The O-acetyl-L-homoserine is then converted to L-methionine and acetate in the presence of a reduced sulphur source, such as methyl mercaptan (MC), and of pyridoxal 5'-phosphate (PLP) by an (heterologous) sulfhydrylase (MetY). Whereas O-acetyl-L-homoserine is one of the natural intermediates of methionine biosynthesis in corynebacteria, methionine biosynthesis in enterobacteria proceeds analogously via an O-succinyl-L-homoserine intermediate (see e.g. Figge R (2007) Methionine biosynthesis in *Escherichia coli* and *Corynebacterium glutamicum*. In: Wendisch VF (ed) Amino acid biosynthesis—pathways, regulation and metabolic engineering. Microbiology Monographs, vol 5. Springer, Berlin, pp 163-193). Therefore, the L-homoserine O-acetyltransferase and O-acetyl-L-homoserine sulfhydrylase activities must first be introduced heterologously in enterobacteria such as *E. coli*, whereas these enzyme activities are naturally already present in corynebacteria such as *C. glutamicum*. The corresponding homologous or heterologous genes encoding the corresponding enzymes can each be enhanced by the measures described at the outset (such as increasing the copy number of both genes and/or the use of strong promoters).

In enterobacteria such as *E. coli*, the enhanced L-homoserine O-acetyltransferase and O-acetyl-L-homoserine sulfhydrylase activities may be introduced by transformation by means of suitable vectors comprising the gene sequences metX (e.g. SEQ ID NO:1) and metY (e.g. SEQ ID NO:3), which in each case is upstream of a strong promoter (for example PtacI). An example of such a construct is the sequence according to sequence number 6 (SEQ ID NO:6).

The acetate liberated by the conversion of O-acetyl-L-homoserine to L-methionine, in the presence of methyl mercaptan (MC) and pyridoxal 5'-phosphate (PLP) and also the (heterologous) sulfhydrylase (MetY), is then used again for the synthesis of acetyl-CoA, with consumption of ATP, in the cytoplasm of *E. coli* (likewise *Bacillus subtilis*) by means of an acetate-inducible acetyl-CoA synthetase (Acs), which is activated particularly in the stationary phase or under anaerobic conditions by the regulator CsrA (S. Kumari et al., JOURNAL OF BACTERIOLOGY, Vol. 177, No. 10, May 1995, p. 2878-2886).

In contrast to *E. coli*, excess acetate in *C. glutamicum* is converted exclusively in an ATP-dependent reaction to acetyl phosphate, by means of an acetate kinase (AK), which finally reacts by means of a phosphotransacetylase (PTA) in the presence of CoA to give acetyl-CoA. The corresponding genes, ack and pta, are organized in *C. glutamicum* in an operon regulated by acetate at the transcriptional level (R. Gerstmeir et al. Journal of Biotechnology 104 (103) 99-122).

L-methionine is excreted out of the cell of *E. coli* by means of the YjeH exporter (Q. Liu et al., Appl Environ Microbiol 81 (2015) p. 7753-7766). Furthermore, the gene ygaZH in *E. coli* encodes a methionine exporter (WO2015/028675 A1). L-methionine is excreted out of the cell of *C. glutamicum* into the culture medium with the aid of the BrnFE exporter (C. Trötschel et al., JOURNAL OF BACTERIOLOGY, June 2005, p. 3786-3794).

FIG. 1 Shows the pMW218 plasmid map.

FIG. 2: Shows the pMW218_Ptac-metX_Ptac-metY plasmid map.

FIG. 3: Shows the catalytic conversion of L-homoserine and acetyl-CoA by the cell homogenates of MG1655/pMW218 or MG1655/pMW218_Ptac-metX_Ptac-metY.

FIG. 4: Shows the catalytic conversion of sodium methyl mercaptide in the presence of O-acetylhomoserine and pyridoxal 5'-phosphate (PLP) by the O-acetylhomoserine sulfhydrylase enzyme (MetY). Comparison of the cell homogenates of MG1655/pMW218 and MG1655/pMW218_Ptac-metX_Ptac-metY is shown with the respective total protein concentrations used.

EXAMPLES

1) Preparation of an Enterobacterium Heterologously Expressing the Genes for an L-Homoserine O-Acetyltransferase and a Sulfhydrylase of a Corynebacteria Species On the basis of the genome sequence of *Corynebacterium glutamicum* (ATCC13032) NC_003450, the gene sequences metX (SEQ ID NO:1) and metY (SEQ ID NO:3), which encode the L-homoserine O-acetyltransferase having the amino acid sequence according to SEQ ID NO:2 and the O-acetyl-L-homoserine sulfhydrylase having the amino acid sequence according to SEQ ID NO:4 respectively, both with upstream promoter PtacI (SEQ ID NO:5) (H. A. deBoer et al., Proc. Natl. Acad. Sci. USA, Vol. 80, 21-25, January 1983, Biochemistry) from Life Technologies Invitrogen GeneArt (Germany), were synthesized (SEQ ID NO:6).

In this SEQ ID NO:6, the PtacI promoter is from base pair 407-447, the gene sequence of metX from 502-1638, the PtacI promoter again from 1645-1685 and the gene sequence of metY from 1742-3055.

Subsequently, the cloning of this synthetic sequence was carried out via the restriction sites BssHII and BglI in the vector sequence pMW218 (Accession Number: AB005477) (Nippon Gene, Toyama, Japan) (FIG. 1). The plasmid pMW218_Ptac-metX_Ptac-metY is formed therefrom (FIG. 2). To analyze the pMW218_Ptac-metX_Ptac-metY plasmid, DNA sequencing was additionally carried out by Eurofins MWG Operon. The DNA sequences obtained were checked with respect to correctness using the Clone Manager software so that the nucleotide sequence SEQ ID NO:6 was confirmed.

The plasmids pMW218 and pMW218_Ptac-metX_Ptac-metY have been transformed in each case in the *Escherichia coli* K-12 strain MG1655 (DSM No. 18039). The transformants were subsequently cultured on LB medium agar plates with 50 µg/ml kanamycin such that the MG1655/pMW218 and MG1655/pMW218_Ptac-metX_Ptac-metY strains could be generated. In each case a colony has been selected which was inoculated in each case into 10 ml of LB medium with 50 µg/ml kanamycin, and was cultured at 37° C., 200 rpm for 6 hours. Subsequently, 10 ml of medium A [25 g/l ammonium sulphate; 1 g/l magnesium sulphate heptahydrate; 2 g/l potassium dihydrogen phosphate; 0.03 g/l iron heptahydrate; 0.02 g/l manganese sulphate monohydrate; 20 g/l glucose monohydrate; 30 g/l calcium carbonate; 0.05 g/l kanamycin; 0.025 g/l pyridoxal phosphate (PLP); 0.0024 g/l isopropyl-β-D-thiogalactopyranoside (IPTG)] were inoculated with 200 µl of the growth cell culture and incubated at 37° C., 200 rpm for 16 h. These cell cultures were diluted with 10 ml of fresh medium A in a 100 ml flask to an OD of 2 and were further cultured under identical conditions until an OD of about 5 had been attained (circa 3-4 h). Subsequently, these cells, which are in the exponential growth phase and have homoserine O-acetyltransferase (MetX) and sulfhydrylase (MetY) activity, can be used for the biotransformation. Biotransformation is understood to mean a substance conversion, in which whole living cells, fixed cells or isolated free or carrier-linked enzymes or the combination of the above are used.

2) Detection of the Enzymatic Activities of L-Homoserine O-Acetyltransferase and Acetyl-L-Homoserine Sulfhydrylase 10 ml of LB medium with 50 µg/ml kanamycin have been inoculated in each case with a single colony of the MG1655/pMW218 and MG1655/pMW218_Ptac-metX_Ptac-metY strains and have been cultured at 37° C., 200 rpm for 6 hours. Subsequently, 10 ml of medium A (see Example 1)

were inoculated with 200 µl of the growth cell culture and incubated at 37° C., 200 rpm for 16 h. The cell cultures were then each harvested (8 ml normalized to an OD=1), the supernatants removed by centrifugation (20 min, 4000 rpm, 4° C.) and the pelleted cells were washed twice with 800 µl of 0.1 M potassium phosphate buffer (pH 7.5) and taken up in 1 ml of buffer. The mechanical cell disruption was carried out in a FastPrep FP120 instrument (QBiogene, Heidelberg), wherein the cells were shaken three times for 20 s at 6.5 m/s in digestion vessels with 300 mg of glass beads (Ø 0.2-0.3 mm). The crude extract was then centrifuged at 12 000 rpm, 4° C., 20 min, in order to remove undigested cells and cell debris. The total amount of protein was determined using the Bio-Rad protein quantification assay (Bio-Rad, USA). The cell homogenate was then used for the enzymatic detection of the cytoplasmatic L-homoserine O-acetyltransferase and acetyl-L-homoserine sulfhydrylase activity.

2a) Detection of the Cytoplasmatic Activity of MetX (L-Homoserine O-Acetyltransferase)

The reaction, which the enzyme L-homoserine O-acetyltransferase (MetX) [EC2.3.1.31] catalyzes, is the conversion of L-homoserine and acetyl-CoA to O-acetyl-L-homoserine and CoA. With the aid of a DTNB solution (5,5'-dithiobis-2-nitrobenzoic acid, "Ellmans reagent", Sigma Aldrich, Germany) the progress of this reaction can be recorded by measurements of absorption at 412 nm, since DTNB forms a yellow substance with the SH group of CoA (S. Yamagata Journal of Bacteriology 169, No. 8 (1987) 3458-3463). The photometric MetX enzyme assay was conducted at 37° C., in which calibration was previously carried out using CoA concentrations between 0-200 µM. Each preparation was conducted in a 0.2 ml reaction mixture with 100 mM potassium phosphate buffer (pH 7.5), 0.65 mM DNTB [100 µl of a 1.3 mM DTNB stock], 0.13 mM acetyl-CoA [30 µl of a 0.886 mM acetyl-CoA stock, Sigma Aldrich, Germany], 10 mM L-homoserine [20 µl of a 100 mM L-homoserine stock, Sigma Aldrich, Germany] and the specified protein concentration of 0.012 mg/ml, or 0.024 mg/ml of the respective cell homogenate.

Since acetyl-CoA is used within the cell for various biosyntheses, diverse enzymes are present in the cytoplasm which catalyze the cleavage of acetyl-CoA to CoA, such that the difference between the cell homogenates with and without MetX needs to be considered.

It was observed as a result of the enzyme assay that the DNTB absorption increase of the cell homogenate of MG1655/pMW218_Ptac-metX_Ptac-metY was constantly above that of MG1655/pMW218 over the time course (FIG. 3). This confirms that MetX here is catalytically active as an additional enzyme. Comparison of the slopes of the initial linear regions of the recorded curves shows activities in the cell homogenate of MG1655/pMW218 of around 580 µmol/min per g of total protein and in MG1655/pMW218_Ptac-metX_Ptac-metY around 730 µmol/min per g of total protein. The difference therefore is the specific activity of the L-homoserine O-acetyltransferase (MetX) at around 150 units per g of total protein (1 unit=1 µmol substrate conversion/min).

2b) Detection of the Cytoplasmic Activity of MetY (O-Acetyl-L-Homoserine Sulfhydrylase)

The reaction, which the enzyme O-acetyl-L-homoserine sulfhydrylase (MetY) [EC 2.5.1.49] catalyzes, is the conversion of O-acetyl-L-homoserine with methanethiol (MC) in the presence of pyridoxal 5'-phosphate (PLP) to give L-methionine and acetate. As described in Example 2a, the progress of this reaction can be determined by means of DTNB absorption measurements at 412 nm, since DTNB reacts with the SH group of unreacted methyl mercaptan to give a yellow substance. For this purpose, the two strains MG1655/pMW218 and MG1655/pMW218_Ptac-metX_Ptac-metY were prepared as cell homogenates as described above and the decrease or the conversion of the substrate sodium methyl mercaptide was measured in the subsequent enzyme assay.

Each preparation was conducted at 37° C. in a 1 ml reaction mixture with 100 mM potassium phosphate buffer (pH 7.5), 2 mM sodium methyl mercaptide (NaMC) [10 µl of a 200 mM NaMC stock], 3 mM OAH HCl [30 µl of a 100 mM OAH HCl stock] and 0.01 mM PLP [10 µl of a 1 mM PLP stock] with the respective cell homogenate at a total protein concentration of 0.012 g/l; 0.024 g/l, or 0.048 g/l. Following the time-limited enzymatic reaction, the photometric measurement of the NaMC content by means of DTNB was conducted, wherein a calibration was previously carried out using MC concentrations between 0-200 µM. For this purpose, 180 µl of a DTNB solution (4 mg/ml) were added to each 20 µl of the enzymatic reaction mixture and subsequently measured at 412 nm.

The presence of the cell homogenate of the MG1655/pMW218_Ptac-metX_Ptac-metY strain leads to the decrease of the NaMC being catalyzed significantly faster than in the presence of the cell homogenate of MG1655/pMW218, due to the enzyme activity of MetY, depending on the total protein concentration (FIG. 4). The decrease of NaMC likewise occurring, but more weakly, in the preparations with the cell homogenate of MG1655/pMW218 is independent of the amount of protein used. An identical decrease could also be observed in a preparation without cell homogenate and is due to the chemically dependent outgassing of the methyl mercaptan occurring from the solutions. From the difference in the slopes in the linear range, a specific MetY sulfhydrylase activity around 1500 units per g of total protein (1 unit=1 µmol substrate conversion/min) can be calculated, which is on the same level as that from the MetX enzyme.

3) Detection of the Cellular Biotransformation of L-Homoserine and Sodium Methyl Mercaptide to Give L-Methionine The MG1655/pMW218 and MG1655/pMW218_Ptac-metX_Ptac-metY strains have been cultured as described in Example 1 and then, in the exponential phase of each preparation, have been adjusted to an OD600 of around 7.

The biotransformation was then carried out in 100 ml shaking flasks at 37° C., 200 rpm over a time period of 0, 2, 4 and 24 h. Each preparation was conducted in 10 ml of medium A with 6.5 g/l L-homoserine [500 µl of a 100 g/l homoserine stock] (Sigma Aldrich, Germany), 3 g/l NaMC [500 µl of a 6% NaMC stock] and 12 g/l $KH_2PO_4$ [600 µl of a 200 g/l $KH_2PO_4$ stock].

The conversion of L-homoserine with methyl mercaptan to give L-methionine was conducted using the MG1655/pMW218_Ptac-metX_Ptac-metY strain, whereas no L-methionine was synthesized using the MG1655/pMW218 strain (Table 1). The various yields based on the amounts of NaMC initially charged and amounts of L-homoserine consumed are based on an equal stoichiometry of both substrates present at the start but subsequent naturally occurring evaporation of the methyl mercaptan.

TABLE 1

Comparison of the biotransformations of 6.5 g/l synthetic L-homoserine
and 3 g/l sodium methyl mercaptide using the MG1655/pMW218 and
MG1655/pMW218_Ptac-metX_Ptac-metY strains.
The L-methionine titre obtained over the time course and the related
yields are shown, based on the amount of NaMC pulsed at the start
and the amount of L-homoserine (L-HS) consumed.

|  | 0 h | 2 h | 4 h | 24 h |
|---|---|---|---|---|
| MG1655/pMW218 | | | | |
| L-Met (g/l) | <0.005 | <0.005 | <0.005 | <0.005 |
| MG1655/pMW218_Ptac-metX_Ptac-metY | | | | |
| L-Met (g/l) | <0.005 | 0.810 | 0.980 | 1.500 |
| L-Homoserine (g/l) | 6.580 | 4.220 | 4.020 | 3.560 |
| L-Met/initially charged NaMC (mol/mol) | 0% | 12.7% | 15.3% | 23.5% |
| L-Met/consumed L-HS (mol/mol) | 0% | 27.4% | 30.6% | 39.7% |

Furthermore, a biotransformation using the MG1655/pMW218_Ptac-metX_Ptac-metY strain has been carried out, in which deuterated NaMC (D$_3$CSNa) was used in place of the NaMC stock from Sigma Aldrich. This was prepared by introducing CD$_3$SD (Sigma-Aldrich, 98 atom % D) into an equimolar amount of aqueous sodium hydroxide solution. (Alternatively, it can be prepared according to J. Voss et al., Phosphorous, Sulfur and Silicon and the Related Elements, 2012, 187, 382 from thiourea and CD$_3$I.) Analysis of the solution after 24 h reaction by LC-MS showed a ratio of methionine to methionine-d-3 of 1:200. It could be detected, therefore, that the methionine formed in the biotransformation is formed exclusively by the incorporation of externally supplied methyl mercaptan.

4) Conversion of L-Homoserine, Produced by Fermentation, to L-Methionine Via a Biotransformation On the basis of the biotransformation of synthetic L-homoserine to L-methionine conducted in Example 3a, the biotransformation of L-homoserine produced by fermentation has also been investigated. The concentration of the L-homoserine broth produced by fermentation was 10 g/l. The MG1655/pMW218_Ptac-metX_Ptac-metY strain has been cultured as in Example 1 and the biotransformation conducted in the exponential phase at an OD of 5 in the presence of 5 g/l L-homoserine produced by fermentation and as described in Example 3a for 2, 4 and 24 h. As shown in Table 2, after two hours' biotransformation around 7%, after four hours around 12% and after 24 hours around 45% of the substrates L-homoserine or NaMC were converted to L-methionine, which was reflected in a maximum titre of around 2.9 g/l L-methionine.

TABLE 2

L-methionine and the related yields formed by the biotransformation
of 5 g/l L-homoserine produced by fermentation and 3 g/l sodium methyl
mercaptide by the MG1655/pMW218_Ptac-metX_Ptac-metY strain.

| | Time (h) | | | |
|---|---|---|---|---|
| | 0 | 2 | 4 | 24 |
| L-Met (g/l) | <0.005 | 0.45 | 0.79 | 2.87 |
| L-Homoserine from fermentation (g/l) | 5.26 | 4.74 | 4.24 | 2.15 |
| L-Met/initially charged NaMC (mol/mol) | 0% | 7% | 12% | 45% |
| L-Met/consumed L-HS (mol/mol) | 0% | 69% | 62% | 74% |

5) Cellular Recycling of Acetate During the Biotransformation

To investigate the amounts of acetate formed in the biotransformation of L-homoserine and methyl mercaptan, preparations using the MG1655/pMW218 and MG1655/pMW218_Ptac-metX_Ptac-metY strains in the presence of 5 g/l L-homoserine and 3 g/l sodium methyl mercaptide and 12 g/l KH$_2$PO$_4$ [600 µl of a 200 g/l KH$_2$PO$_4$ stock] were documented over four hours with respect to their acetate content.

The MG1655/pMW218 and MG1655/pMW218_Ptac-metX_Ptac-metY strains have been prepared as described in Example 1, so that an exponential culture having a starting OD of around 3 was used for the respective 10 ml preparations in 100 ml flasks as described in Example 3b.

The acetate concentrations which are formed during the biotransformation of 5 g/l L-homoserine and 3 g/l sodium methyl mercaptide by the MG1655/pMW218 and MG1655/pMW218_Ptac-metX_Ptac-metY strains are documented in Table 3. L-methionine is formed only in the preparation with the strain heterologously expressing the metX and metY genes, whereas in the preparation with the control strain MG1655/pMW218 no L-methionine was detectable.

Within the first four hours around 11 mM acetate are formed due to the experimental parameters in the control preparation, whereas in the biotransformation around 17 mM acetate and 7 Mm L-methionine are formed. The excess of acetate measured in the biotransformation preparation which gives rise to the difference is thus 6 mM. Due to the additional methionine synthesis with an equimolar production of acetate and methionine, which is not described for non-cellular systems (WO 2008/013432 A1), this value would be 7 mM. Therefore, a cellular recycling of the acetate formed in the L-methionine synthesis in the biotransformation could be detected. The additional acetate resulting from the biotransformation has therefore obviously been partly recycled by the acetyl-CoA synthetase (Acs) to acetyl-CoA.

TABLE 3

Formation and recycling of acetate in biotransformation preparations with
the MG1655/pMW218 and MG1655/pMW218_Ptac-metX_Ptac-metY strains
in the presence of 5 g/l L-homoserine and 3 g/l sodium methyl mercaptide.

| Time [h] | MG1655/pMW_Ptac-metX_Ptac-metY L-Met [mM] | MG1655/pMW_Ptac-metX_Ptac-metY Acetate [mM] | MG1655/pMW218 Acetate [mM] | Excess acetate [mM] | Amount of acetate expected (equimolar to L-Met) [mM] | Recycled acetate [mM] |
|---|---|---|---|---|---|---|
| 0 | <0.03 | <0.08 | <0.08 | 0.00 | 0.00 | 0.00 |
| 2 | 4.76 | 10.29 | 7.54 | 2.75 | 4.76 | 2.01 |
| 4 | 7.37 | 17.45 | 11.22 | 6.22 | 7.37 | 1.15 |

6) External Addition of L-Homoserine

The MG1655/pMW218 and MG1655/pMW218_Ptac-metX_Ptac-metY strains have been prepared as described in Example 1, so that an exponential culture having a starting OD of around 3 was used for the respective 10 ml preparations in 100 ml flasks as described in Example 3b. To the respective preparations followed at the 0 h time point firstly no addition, the addition of 5 g/l L-homoserine, the addition of 3 g/l sodium methyl mercaptide with 12 g/l $KH_2PO_4$ [600 µl of a 200 g/l $KH_2PO_4$ stock] and the addition of 5 g/l L-homoserine with 3 g/l sodium methyl mercaptide and 12 g/l $KH_2PO_4$ [600 µl of a 200 g/l $KH_2PO_4$ stock].

The L-methionine and L-homoserine titres of the preparations were determined at the time points 0, 2, 4 and 6 h.

TABLE 4

L-methionine and L-homoserine titres after the external addition of 5 g/l L-homoserine (L-HS) to the biotransformation preparations using the MG1655/pMW218 and MG1655/pMW218_Ptac-metX_Ptac-metY strains in the presence and absence of 3 g/l sodium methyl mercaptide (Na-MC).

| Time [h] | Addition L-HS | Na-MC addition | MG1655/pMW_Ptac-metX_Ptac-metY | | MG1655/pMW218 | |
|---|---|---|---|---|---|---|
| | | | L-Methionine [g/l] | L-Homoserine [g/l] | L-Methionine [g/l] | L-Homoserine [g/l] |
| 0 | — | — | <0.005 | <0.005 | <0.005 | <0.005 |
| 2 | — | — | <0.005 | <0.005 | <0.005 | <0.005 |
| 4 | — | — | <0.005 | <0.005 | <0.005 | <0.005 |
| 6 | — | — | <0.005 | <0.005 | <0.005 | <0.005 |
| 24 | — | — | <0.005 | <0.005 | <0.005 | <0.005 |
| 0 | 5 g/l | — | <0.005 | 5.38 | <0.005 | 5.34 |
| 2 | — | — | <0.005 | 4.09 | <0.005 | 5.08 |
| 4 | — | — | <0.005 | 2.35 | <0.005 | 4.77 |
| 6 | — | — | <0.005 | 1.51 | <0.005 | 4.46 |
| 24 | — | — | <0.005 | <0.005 | <0.005 | 3.52 |
| 0 | — | 3 g/l | <0.005 | <0.005 | <0.005 | <0.005 |
| 2 | — | — | <0.005 | <0.005 | <0.005 | <0.005 |
| 4 | — | — | 0.22 | <0.005 | <0.005 | <0.005 |
| 6 | — | — | 0.27 | <0.005 | <0.005 | <0.005 |
| 24 | — | — | 0.28 | <0.005 | <0.005 | <0.005 |
| 0 | 5 g/l | 3 g/l | <0.005 | 5.01 | <0.005 | 5.31 |
| 2 | | | 0.71 | 4.44 | <0.005 | 5.09 |
| 4 | | | 1.10 | 4.11 | <0.005 | 4.89 |
| 6 | | | 1.24 | 4.06 | <0.005 | 4.65 |
| 24 | | | 1.46 | 3.56 | <0.005 | 3.98 |

7) Biotransformation of L-Homoserine and Dimethyl Disulfide (DMDS) or of L-Homoserine and Sodium Methylmercaptide (NaMC) to Give L-Methionine The MG1655/pMW218_Ptac-metX_Ptac-metY strain has been cultured as described in Example 1 and then, in the exponential phase of each preparation, has been adjusted to an OD600 of around 10.

The biotransformation was then carried out in 100 ml shaking flasks at 37° C., 200 rpm over a time period of 0, 24 and 48 h. Each preparation was conducted in 10 ml of medium A (see Example 1) with 5.0 g/l L-homoserine and 12 g/l $KH_2PO_4$ [600 µl of a 200 g/l $KH_2PO_4$ stock] and the quantities of the sulphur source (i.e. NaMC or DMDS) as provided in Table 5. The control did not contain any sulphur source (i.e. no NaMC and no DMDS).

TABLE 5

Comparison of the results of the biotransformation with NaMC, control (no sulphur source) and DMDS at different concentrations and reaction time periods

| Sulphur source concentration, reaction time | L-Homoserine [g/l] | L-Methionine [g/l] | O-Acetyl-L-homoserine [g/l] |
|---|---|---|---|
| 1.0 g/L NaMC, 24 h | 3.52 | 1.64 | <0.005 |
| Control, 0 h | 4.9 | <0.005 | <0.005 |
| Control, 24 h | 1.48 | <0.005 | 3.74 |
| 0.5 g/L DMDS, 24 h | 2.3 | 0.2 | 2.82 |
| 1 g/L DMDS, 24 h | 2.48 | 0.32 | 2.34 |
| 1 g/L DMDS, 48 h | 2.52 | 0.46 | 2.06 |
| 2 g/L DMDS, 24 h | 3.3 | 0.42 | 1.38 |

The invention claimed is:

1. A method of producing L-methionine, comprising: culturing a microorganism selected from the group consisting of: *Escherichia coli, Corynebacterium glutamicum*, and *Corynebacterium humireducens* in a culture medium which, at the start of culturing, comprises L-homoserine and a sulphur source selected from the group consisting of: methyl mercaptan, a methyl mercaptan salt and dimethyl disulfide, wherein said culturing results in the accumulation of said L-methionine in said culture medium, and wherein:
 the microorganism has been genetically engineered to increase, compared to the microorganism prior to genetic engineering, the activity of:
 i) an enzyme having L-homoserine O-acetyltransferase activity and comprising the amino acid sequence of SEQ ID NO:2; and
 ii) an enzyme having O-acetyl-L-homoserine sulfhydrylase activity and comprising the amino acid sequence of SEQ ID NO:4;
 by increasing the copy number of nucleotide sequences encoding the enzymes and/or due to nucleotide sequences encoding the enzymes being in functional linkage to a promoter that increases expression of the enzymes; and
 during culturing, acetate formed as a result of conversion of O-acetyl-L-homoserine to L-methionine is reused by the microorganism that has been genetically engineered.

2. The method of claim 1, wherein said L-homoserine O-acetyltransferase activity is encoded by a gene comprising the coding sequence of SEQ ID NO:1.

3. The method of claim 1, wherein said O-acetyl-L-homoserine sulfhydrylase activity is encoded by a gene comprising the coding sequence of SEQ ID NO:3.

4. The method of claim 1, wherein the increase in the activity of both the L-homoserine O-acetyltransferase and the O-acetyl-L-homoserine sulfhydrylase is due to an increase in the copy number of nucleotide sequences encoding these enzymes.

5. The method of claim 1, wherein the increase in the activity of both the L-homoserine O-acetyltransferase and the O-acetyl-L-homoserine sulfhydrylase is due to nucleotide sequences encoding these enzymes being in functional linkage to a promoter that increases expression.

6. The method of claim 5, wherein said promoter is selected from the group consisting of: a tacI promoter (PtacI) comprising the sequence of SEQ ID NO:5; a glucose dependent deo promoter; a tac promoter; a lac promoter; a trp promoter; an *Escherichia coli* lac operon inducible by lactose or isopropyl ß-D-thiogalactopyranoside; systems using arabinose or rhamnose as inducers; an *Escherichia coli* cspA promoter; a Lambda PL promoter; and an osmB promoter.

7. The method of claim 1, wherein at the start of culturing, homoserine is present in the culture medium at about 3.5 g/l to about 6.6 g/l.

8. The method of claim 1, wherein the amino acid sequence of the enzyme having L-homoserine O-acetyltransferase activity, consists essentially of the amino acid sequence of SEQ ID NO:2.

9. The method of claim 1, wherein the amino acid sequence of the enzyme having L-homoserine O-acetyltransferase activity, consists of the amino acid sequence of SEQ ID NO:2.

10. The method of claim 1, wherein the amino acid sequence of the enzyme having O-acetyl-L-homoserine sulfhydrylase activity consists essentially of the amino acid sequence of SEQ ID NO:4.

11. The method of claim 1, wherein the amino acid sequence of the enzyme having O-acetyl-L-homoserine sulfhydrylase activity consists of the amino acid sequence of SEQ ID NO:4.

12. The method of claim 8, wherein the amino acid sequence of the enzyme having O-acetyl-L-homoserine sulfhydrylase activity consists essentially of the amino acid sequence of SEQ ID NO:4.

13. The method of claim 9, wherein the amino acid sequence of the enzyme having O-acetyl-L-homoserine sulfhydrylase activity consists of the amino acid sequence of SEQ ID NO:4.

14. The method of claim 13, wherein the increase in activity of both the enzyme of i) and the enzyme of ii) is due to an increase in the copy number of nucleotide sequences encoding said enzyme.

15. The method of claim 13, wherein the increase in activity of both the enzyme of i) and the enzyme of ii) is due to nucleotide sequences encoding said enzyme being in functional linkage to a promoter that increases expression.

16. The method of claim 15, wherein said promoter is selected from the group consisting of: a tacI promoter (PtacI) comprising the sequence of SEQ ID NO:5; a glucose dependent deo promoter; a tac promoter; a lac promoter; a trp promoter; an *Escherichia coli* lac operon inducible by lactose or isopropyl ß-D-thiogalactopyranoside; systems using arabinose or rhamnose as inducers; an *Escherichia coli* cspA promoter; a Lambda PL promoter; and an osmB promoter.

* * * * *

SEQUENCE LISTING

<160> NUMBER OF SEQ ID NOS: 6

<210> SEQ ID NO 1
<211> LENGTH: 1137
<212> TYPE: DNA
<213> ORGANISM: Corynebacterium glutamicum
<220> FEATURE:
<221> NAME/KEY: CDS
<222> LOCATION: (1)..(1137)
<223> OTHER INFORMATION: metX

<400> SEQUENCE: 1

| | | | | | | | | | | | | | | | | |
|---|---|---|---|---|---|---|---|---|---|---|---|---|---|---|---|---|
| atg | ccc | acc | ctc | gcg | cct | tca | ggt | caa | ctt | gaa | atc | caa | gcg | atc | ggt | 48 |
| Met | Pro | Thr | Leu | Ala | Pro | Ser | Gly | Gln | Leu | Glu | Ile | Gln | Ala | Ile | Gly | |
| 1 | | | | 5 | | | | | 10 | | | | | 15 | | |

| gat | gtc | tcc | acc | gaa | gcc | gga | gca | atc | att | aca | aac | gct | gaa | atc | gcc | 96 |
|---|---|---|---|---|---|---|---|---|---|---|---|---|---|---|---|---|
| Asp | Val | Ser | Thr | Glu | Ala | Gly | Ala | Ile | Ile | Thr | Asn | Ala | Glu | Ile | Ala | |
| | | | 20 | | | | | 25 | | | | | 30 | | | |

| tat | cac | cgc | tgg | ggt | gaa | tac | cgc | gta | gat | aaa | gaa | gga | cgc | agc | aat | 144 |
|---|---|---|---|---|---|---|---|---|---|---|---|---|---|---|---|---|
| Tyr | His | Arg | Trp | Gly | Glu | Tyr | Arg | Val | Asp | Lys | Glu | Gly | Arg | Ser | Asn | |
| | | 35 | | | | | 40 | | | | | 45 | | | | |

| gtc | gtt | ctc | atc | gaa | cac | gcc | ctc | act | gga | gat | tcc | aac | gca | gcc | gat | 192 |
|---|---|---|---|---|---|---|---|---|---|---|---|---|---|---|---|---|
| Val | Val | Leu | Ile | Glu | His | Ala | Leu | Thr | Gly | Asp | Ser | Asn | Ala | Ala | Asp | |
| 50 | | | | | 55 | | | | | 60 | | | | | | |

| tgg | tgg | gct | gac | ttg | ctc | ggt | ccc | ggc | aaa | gcc | atc | aac | act | gat | att | 240 |
|---|---|---|---|---|---|---|---|---|---|---|---|---|---|---|---|---|
| Trp | Trp | Ala | Asp | Leu | Leu | Gly | Pro | Gly | Lys | Ala | Ile | Asn | Thr | Asp | Ile | |
| 65 | | | | | 70 | | | | | 75 | | | | | 80 | |

| tac | tgc | gtg | atc | tgt | acc | aac | gtc | atc | ggt | ggt | tgc | aac | ggt | tcc | acc | 288 |
|---|---|---|---|---|---|---|---|---|---|---|---|---|---|---|---|---|
| Tyr | Cys | Val | Ile | Cys | Thr | Asn | Val | Ile | Gly | Gly | Cys | Asn | Gly | Ser | Thr | |
| | | | 85 | | | | | 90 | | | | | 95 | | | |

| gga | cct | ggc | tcc | atg | cat | cca | gat | gga | aat | ttc | tgg | ggt | aat | cgc | ttc | 336 |
|---|---|---|---|---|---|---|---|---|---|---|---|---|---|---|---|---|
| Gly | Pro | Gly | Ser | Met | His | Pro | Asp | Gly | Asn | Phe | Trp | Gly | Asn | Arg | Phe | |
| | | | 100 | | | | | 105 | | | | | 110 | | | |

| ccc | gcc | acg | tcc | att | cgt | gat | cag | gta | aac | gcc | gaa | aaa | caa | ttc | ctc | 384 |
|---|---|---|---|---|---|---|---|---|---|---|---|---|---|---|---|---|
| Pro | Ala | Thr | Ser | Ile | Arg | Asp | Gln | Val | Asn | Ala | Glu | Lys | Gln | Phe | Leu | |
| | | 115 | | | | | 120 | | | | | 125 | | | | |

| gac | gca | ctc | ggc | atc | acc | acg | gtc | gcc | gca | gta | ctt | ggt | ggt | tcc | atg | 432 |
|---|---|---|---|---|---|---|---|---|---|---|---|---|---|---|---|---|
| Asp | Ala | Leu | Gly | Ile | Thr | Thr | Val | Ala | Ala | Val | Leu | Gly | Gly | Ser | Met | |
| | 130 | | | | | 135 | | | | | 140 | | | | | |

| ggt | ggt | gcc | cgc | acc | cta | gag | tgg | gcc | gca | atg | tac | cca | gaa | act | gtt | 480 |
|---|---|---|---|---|---|---|---|---|---|---|---|---|---|---|---|---|
| Gly | Gly | Ala | Arg | Thr | Leu | Glu | Trp | Ala | Ala | Met | Tyr | Pro | Glu | Thr | Val | |
| 145 | | | | | 150 | | | | | 155 | | | | | 160 | |

| ggc | gca | gct | gct | gtt | ctt | gca | gtt | tct | gca | cgc | gcc | agc | gcc | tgg | caa | 528 |
|---|---|---|---|---|---|---|---|---|---|---|---|---|---|---|---|---|
| Gly | Ala | Ala | Ala | Val | Leu | Ala | Val | Ser | Ala | Arg | Ala | Ser | Ala | Trp | Gln | |
| | | | | 165 | | | | | 170 | | | | | 175 | | |

| atc | ggc | att | caa | tcc | gcc | caa | att | aag | gcg | att | gaa | aac | gac | cac | cac | 576 |
|---|---|---|---|---|---|---|---|---|---|---|---|---|---|---|---|---|
| Ile | Gly | Ile | Gln | Ser | Ala | Gln | Ile | Lys | Ala | Ile | Glu | Asn | Asp | His | His | |
| | | | 180 | | | | | 185 | | | | | 190 | | | |

| tgg | cac | gaa | ggc | aac | tac | tac | gaa | tcc | ggc | tgc | aac | cca | gcc | acc | gga | 624 |
|---|---|---|---|---|---|---|---|---|---|---|---|---|---|---|---|---|
| Trp | His | Glu | Gly | Asn | Tyr | Tyr | Glu | Ser | Gly | Cys | Asn | Pro | Ala | Thr | Gly | |
| | | | 195 | | | | | 200 | | | | | 205 | | | |

| ctc | ggc | gcc | gcc | cga | cgc | atc | gcc | cac | ctc | acc | tac | cgt | ggc | gaa | cta | 672 |
|---|---|---|---|---|---|---|---|---|---|---|---|---|---|---|---|---|
| Leu | Gly | Ala | Ala | Arg | Arg | Ile | Ala | His | Leu | Thr | Tyr | Arg | Gly | Glu | Leu | |
| | 210 | | | | | 215 | | | | | 220 | | | | | |

| gaa | atc | gac | gaa | cgc | ttc | ggc | acc | aaa | gcc | caa | aag | aac | gaa | aac | cca | 720 |
|---|---|---|---|---|---|---|---|---|---|---|---|---|---|---|---|---|
| Glu | Ile | Asp | Glu | Arg | Phe | Gly | Thr | Lys | Ala | Gln | Lys | Asn | Glu | Asn | Pro | |
| 225 | | | | | 230 | | | | | 235 | | | | | 240 | |

| ctc | ggt | ccc | tac | cgc | aag | ccc | gac | cag | cgc | ttc | gcc | gtg | gaa | tcc | tac | 768 |
|---|---|---|---|---|---|---|---|---|---|---|---|---|---|---|---|---|
| Leu | Gly | Pro | Tyr | Arg | Lys | Pro | Asp | Gln | Arg | Phe | Ala | Val | Glu | Ser | Tyr | |
| | | | | 245 | | | | | 250 | | | | | 255 | | |

| ttg | gac | tac | caa | gca | gac | aag | cta | gta | cag | cgt | ttc | gac | gcc | ggc | tcc | 816 |

```
                Leu Asp Tyr Gln Ala Asp Lys Leu Val Gln Arg Phe Asp Ala Gly Ser
                            260                 265                 270 tac gtc ttg ctc acc gac gcc ctc aac cgc cac gac att ggt cgc gac          864
Tyr Val Leu Leu Thr Asp Ala Leu Asn Arg His Asp Ile Gly Arg Asp
            275                 280                 285 cgc gga ggc ctc aac aag gca ctc gaa tcc atc aaa gtt cca gtc ctt          912
Arg Gly Gly Leu Asn Lys Ala Leu Glu Ser Ile Lys Val Pro Val Leu
        290                 295                 300 gtc gca ggc gta gat acc gat att ttg tac ccc tac cac cag caa gaa          960
Val Ala Gly Val Asp Thr Asp Ile Leu Tyr Pro Tyr His Gln Gln Glu
305                 310                 315                 320 cac ctc tcc aga aac ctg gga aat cta ctg gca atg gca aaa atc gta         1008
His Leu Ser Arg Asn Leu Gly Asn Leu Leu Ala Met Ala Lys Ile Val
                325                 330                 335 tcc cct gtc ggc cac gat gct ttc ctc acc gaa agc cgc caa atg gat         1056
Ser Pro Val Gly His Asp Ala Phe Leu Thr Glu Ser Arg Gln Met Asp
            340                 345                 350 cgc atc gtg agg aac ttc ttc agc ctc atc tcc cca gac gaa gac aac         1104
Arg Ile Val Arg Asn Phe Phe Ser Leu Ile Ser Pro Asp Glu Asp Asn
        355                 360                 365 cct tcg acc tac atc gag ttc tac atc taa tag                              1137
Pro Ser Thr Tyr Ile Glu Phe Tyr Ile
    370                 375

<210> SEQ ID NO 2
<211> LENGTH: 377
<212> TYPE: PRT
<213> ORGANISM: Corynebacterium glutamicum

<400> SEQUENCE: 2

Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Met Tyr Pro Glu Thr Val
145                 150                 155                 160

Gly Ala Ala Ala Val Leu Ala Val Ser Ala Arg Ala Ser Ala Trp Gln
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
```

```
                 210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
                260                 265                 270

Tyr Val Leu Leu Thr Asp Ala Leu Asn Arg His Asp Ile Gly Arg Asp
            275                 280                 285

Arg Gly Gly Leu Asn Lys Ala Leu Glu Ser Ile Lys Val Pro Val Leu
        290                 295                 300

Val Ala Gly Val Asp Thr Asp Ile Leu Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
                340                 345                 350

Arg Ile Val Arg Asn Phe Phe Ser Leu Ile Ser Pro Asp Glu Asp Asn
            355                 360                 365

Pro Ser Thr Tyr Ile Glu Phe Tyr Ile
        370                 375

<210> SEQ ID NO 3
<211> LENGTH: 1314
<212> TYPE: DNA
<213> ORGANISM: Corynebacterium glutamicum
<220> FEATURE:
<221> NAME/KEY: CDS
<222> LOCATION: (1)..(1314)
<223> OTHER INFORMATION: metY

<400> SEQUENCE: 3 atg cca aag tac gac aat tcc aat gct gac cag tgg ggc ttt gaa acc      48
Met Pro Lys Tyr Asp Asn Ser Asn Ala Asp Gln Trp Gly Phe Glu Thr
1               5                   10                  15 cgc tcc att cac gca ggc cag tca gta gac gca cag acc agc gca cga      96
Arg Ser Ile His Ala Gly Gln Ser Val Asp Ala Gln Thr Ser Ala Arg
            20                  25                  30 aac ctt ccg atc tac caa tcc acc gct ttc gtg ttc gac tcc gct gag     144
Asn Leu Pro Ile Tyr Gln Ser Thr Ala Phe Val Phe Asp Ser Ala Glu
        35                  40                  45 cac gcc aag cag cgt ttc gca ctt gag gat cta ggc cct gtt tac tcc     192
His Ala Lys Gln Arg Phe Ala Leu Glu Asp Leu Gly Pro Val Tyr Ser
    50                  55                  60 cgc ctc acc aac cca acc gtt gag gct ttg gaa aac cgc atc gct tcc     240
Arg Leu Thr Asn Pro Thr Val Glu Ala Leu Glu Asn Arg Ile Ala Ser
65                  70                  75                  80 ctc gaa ggt ggc gtc cac gct gta gcg ttc tcc tcc gga cag gcc gca     288
Leu Glu Gly Gly Val His Ala Val Ala Phe Ser Ser Gly Gln Ala Ala
                85                  90                  95 acc acc aac gcc att ttg aac ctg gca gga gcg ggc gac cac atc gtc     336
Thr Thr Asn Ala Ile Leu Asn Leu Ala Gly Ala Gly Asp His Ile Val
            100                 105                 110 acc tcc cca cgc ctc tac ggt ggc acc gag act cta ttc ctt atc act     384
Thr Ser Pro Arg Leu Tyr Gly Gly Thr Glu Thr Leu Phe Leu Ile Thr
        115                 120                 125 ctt aac cgc ctg ggt atc gat gtt tcc ttc gtg gaa aac ccc gac gac     432
Leu Asn Arg Leu Gly Ile Asp Val Ser Phe Val Glu Asn Pro Asp Asp
    130                 135                 140
```

```
cct gag tcc tgg cag gca gcc gtt cag cca aac acc aaa gca ttc ttc    480
Pro Glu Ser Trp Gln Ala Ala Val Gln Pro Asn Thr Lys Ala Phe Phe
145                 150                 155                 160 ggc gag act ttc gcc aac cca cag gca gac gtc ctg gat att cct gcg    528
Gly Glu Thr Phe Ala Asn Pro Gln Ala Asp Val Leu Asp Ile Pro Ala
                165                 170                 175 gtg gct gaa gtt gcg cac cgc aac agc gtt cca ctg atc atc gac aac    576
Val Ala Glu Val Ala His Arg Asn Ser Val Pro Leu Ile Ile Asp Asn
            180                 185                 190 acc atc gct acc gca gcg ctc gtg cgc ccg ctc gag ctc ggc gca gac    624
Thr Ile Ala Thr Ala Ala Leu Val Arg Pro Leu Glu Leu Gly Ala Asp
        195                 200                 205 gtt gtc gtc gct tcc ctc acc aag ttc tac acc ggc aac ggc tcc gga    672
Val Val Val Ala Ser Leu Thr Lys Phe Tyr Thr Gly Asn Gly Ser Gly
    210                 215                 220 ctg ggc ggc gtg ctt atc gac ggc gga aag ttc gat tgg act gtc gaa    720
Leu Gly Gly Val Leu Ile Asp Gly Gly Lys Phe Asp Trp Thr Val Glu
225                 230                 235                 240 aag gat gga aag cca gta ttc ccc tac ttc gtc act cca gat gct gct    768
Lys Asp Gly Lys Pro Val Phe Pro Tyr Phe Val Thr Pro Asp Ala Ala
                245                 250                 255 tac cac gga ttg aag tac gca gac ctt ggt gca cca gcc ttc ggc ctc    816
Tyr His Gly Leu Lys Tyr Ala Asp Leu Gly Ala Pro Ala Phe Gly Leu
            260                 265                 270 aag gtt cgc gtt ggc ctt cta cgc gac acc ggc tcc acc ctc tcc gca    864
Lys Val Arg Val Gly Leu Leu Arg Asp Thr Gly Ser Thr Leu Ser Ala
        275                 280                 285 ttc aac gca tgg gct gca gtc cag ggc atc gac acc ctt tcc ctg cgc    912
Phe Asn Ala Trp Ala Ala Val Gln Gly Ile Asp Thr Leu Ser Leu Arg
    290                 295                 300 ctg gag cgc cac aac gaa aac gcc atc aag gtt gca gaa ttc ctc aac    960
Leu Glu Arg His Asn Glu Asn Ala Ile Lys Val Ala Glu Phe Leu Asn
305                 310                 315                 320 aac cac gag aag gtg gaa aag gtt aac ttc gca ggc ctg aag gat tcc   1008
Asn His Glu Lys Val Glu Lys Val Asn Phe Ala Gly Leu Lys Asp Ser
                325                 330                 335 cct tgg tac gca acc aag gaa aag ctt ggc ctg aag tac acc ggc tcc   1056
Pro Trp Tyr Ala Thr Lys Glu Lys Leu Gly Leu Lys Tyr Thr Gly Ser
            340                 345                 350 gtt ctc acc ttc gag atc aag ggc ggc aag gat gag gct tgg gca ttt   1104
Val Leu Thr Phe Glu Ile Lys Gly Gly Lys Asp Glu Ala Trp Ala Phe
        355                 360                 365 atc gac gcc ctg aag cta cac tcc aac ctt gca aac atc ggc gat gtt   1152
Ile Asp Ala Leu Lys Leu His Ser Asn Leu Ala Asn Ile Gly Asp Val
    370                 375                 380 cgc tcc ctc gtt gtt cac cca gca acc acc cat tca cag tcc gac       1200
Arg Ser Leu Val Val His Pro Ala Thr Thr His Ser Gln Ser Asp
385                 390                 395                 400 gaa gct ggc ctg gca cgc gcg ggc gtt acc cag tcc acc gtc cgc ctg   1248
Glu Ala Gly Leu Ala Arg Ala Gly Val Thr Gln Ser Thr Val Arg Leu
                405                 410                 415 tcc gtt ggc atc gag acc att gat gat atc atc gct gac ctc gaa ggc   1296
Ser Val Gly Ile Glu Thr Ile Asp Asp Ile Ile Ala Asp Leu Glu Gly
            420                 425                 430 ggc ttt gct gca atc tag                                           1314
Gly Phe Ala Ala Ile
        435
```

<210> SEQ ID NO 4

```
<211> LENGTH: 437
<212> TYPE: PRT
<213> ORGANISM: Corynebacterium glutamicum

<400> SEQUENCE: 4
```

| | | | | | | | | | | | | | | |
|---|---|---|---|---|---|---|---|---|---|---|---|---|---|---|
| Met | Pro | Lys | Tyr | Asp | Asn | Ser | Asn | Ala | Asp | Gln | Trp | Gly | Phe | Glu | Thr |
| 1 | | | | 5 | | | | | 10 | | | | | 15 | |
| Arg | Ser | Ile | His | Ala | Gly | Gln | Ser | Val | Asp | Ala | Gln | Thr | Ser | Ala | Arg |
| | | | 20 | | | | | 25 | | | | | 30 | | |
| Asn | Leu | Pro | Ile | Tyr | Gln | Ser | Thr | Ala | Phe | Val | Phe | Ser | Ala | Glu | |
| | | | 35 | | | | | 40 | | | | | 45 | | |
| His | Ala | Lys | Gln | Arg | Phe | Ala | Leu | Glu | Asp | Leu | Gly | Pro | Val | Tyr | Ser |
| | 50 | | | | | 55 | | | | | 60 | | | | |
| Arg | Leu | Thr | Asn | Pro | Thr | Val | Glu | Ala | Leu | Glu | Asn | Arg | Ile | Ala | Ser |
| 65 | | | | | 70 | | | | | 75 | | | | | 80 |
| Leu | Glu | Gly | Gly | Val | His | Ala | Val | Ala | Phe | Ser | Ser | Gly | Gln | Ala | Ala |
| | | | | 85 | | | | | 90 | | | | | 95 | |
| Thr | Thr | Asn | Ala | Ile | Leu | Asn | Leu | Ala | Gly | Ala | Gly | Asp | His | Ile | Val |
| | | | 100 | | | | | 105 | | | | | 110 | | |
| Thr | Ser | Pro | Arg | Leu | Tyr | Gly | Gly | Thr | Glu | Thr | Leu | Phe | Leu | Ile | Thr |
| | | | 115 | | | | | 120 | | | | | 125 | | |
| Leu | Asn | Arg | Leu | Gly | Ile | Asp | Val | Ser | Phe | Val | Glu | Asn | Pro | Asp | Asp |
| | 130 | | | | | 135 | | | | | 140 | | | | |
| Pro | Glu | Ser | Trp | Gln | Ala | Ala | Val | Gln | Pro | Asn | Thr | Lys | Ala | Phe | Phe |
| 145 | | | | | 150 | | | | | 155 | | | | | 160 |
| Gly | Glu | Thr | Phe | Ala | Asn | Pro | Gln | Ala | Asp | Val | Leu | Asp | Ile | Pro | Ala |
| | | | | 165 | | | | | 170 | | | | | 175 | |
| Val | Ala | Glu | Val | Ala | His | Arg | Asn | Ser | Val | Pro | Leu | Ile | Ile | Asp | Asn |
| | | | 180 | | | | | 185 | | | | | 190 | | |
| Thr | Ile | Ala | Thr | Ala | Ala | Leu | Val | Arg | Pro | Leu | Glu | Leu | Gly | Ala | Asp |
| | | | 195 | | | | | 200 | | | | | 205 | | |
| Val | Val | Val | Ala | Ser | Leu | Thr | Lys | Phe | Tyr | Thr | Gly | Asn | Gly | Ser | Gly |
| | 210 | | | | | 215 | | | | | 220 | | | | |
| Leu | Gly | Gly | Val | Leu | Ile | Asp | Gly | Gly | Lys | Phe | Asp | Trp | Thr | Val | Glu |
| 225 | | | | | 230 | | | | | 235 | | | | | 240 |
| Lys | Asp | Gly | Lys | Pro | Val | Phe | Pro | Tyr | Phe | Val | Thr | Pro | Asp | Ala | Ala |
| | | | | 245 | | | | | 250 | | | | | 255 | |
| Tyr | His | Gly | Leu | Lys | Tyr | Ala | Asp | Leu | Gly | Ala | Pro | Ala | Phe | Gly | Leu |
| | | | 260 | | | | | 265 | | | | | 270 | | |
| Lys | Val | Arg | Val | Gly | Leu | Leu | Arg | Asp | Thr | Gly | Ser | Thr | Leu | Ser | Ala |
| | | | 275 | | | | | 280 | | | | | 285 | | |
| Phe | Asn | Ala | Trp | Ala | Ala | Val | Gln | Gly | Ile | Asp | Thr | Leu | Ser | Leu | Arg |
| | 290 | | | | | 295 | | | | | 300 | | | | |
| Leu | Glu | Arg | His | Asn | Glu | Asn | Ala | Ile | Lys | Val | Ala | Glu | Phe | Leu | Asn |
| 305 | | | | | 310 | | | | | 315 | | | | | 320 |
| Asn | His | Glu | Lys | Val | Glu | Lys | Val | Asn | Phe | Ala | Gly | Leu | Lys | Asp | Ser |
| | | | | 325 | | | | | 330 | | | | | 335 | |
| Pro | Trp | Tyr | Ala | Thr | Lys | Glu | Lys | Leu | Gly | Leu | Lys | Tyr | Thr | Gly | Ser |
| | | | 340 | | | | | 345 | | | | | 350 | | |
| Val | Leu | Thr | Phe | Glu | Ile | Lys | Gly | Gly | Lys | Asp | Glu | Ala | Trp | Ala | Phe |
| | | | 355 | | | | | 360 | | | | | 365 | | |
| Ile | Asp | Ala | Leu | Lys | Leu | His | Ser | Asn | Leu | Ala | Asn | Ile | Gly | Asp | Val |
| | 370 | | | | | 375 | | | | | 380 | | | | |
| Arg | Ser | Leu | Val | Val | His | Pro | Ala | Thr | Thr | Thr | His | Ser | Gln | Ser | Asp |

```
                385                 390                 395                 400
            Glu Ala Gly Leu Ala Arg Ala Gly Val Thr Gln Ser Thr Val Arg Leu
                            405                 410                 415

Ser Val Gly Ile Glu Thr Ile Asp Asp Ile Ile Ala Asp Leu Glu Gly
                        420                 425                 430

Gly Phe Ala Ala Ile
                    435

<210> SEQ ID NO 5
<211> LENGTH: 41
<212> TYPE: DNA
<213> ORGANISM: Artificial Sequence
<220> FEATURE:
<223> OTHER INFORMATION: Hybrid promoter (PtacI)

<400> SEQUENCE: 5
gagctgttga caattaatca tcggctcgta taatgtgtgg a                              41

<210> SEQ ID NO 6
<211> LENGTH: 3255
<212> TYPE: DNA
<213> ORGANISM: Artificial Sequence
<220> FEATURE:
<223> OTHER INFORMATION: Synthesized sequence

<400> SEQUENCE: 6
cgcgcatgcc cgacggcgag gatctcgtcg tgacccatgg cgatgcctgc ttgccgaata        60
tcatggtgga aaatggccgc ttttctggat tcatcgactg tggccggctg ggtgtggcgg       120
accgctatca ggacatagcg ttggctaccc gtgatattgc tgaagagctt ggcggcgaat       180
gggctgaccg cttcctcgtg ctttacggta tcgccgctcc cgattcgcag cgcatcgcct       240
tctatcgcct tcttgacgag ttcttctgag cgggactctg gggttcggca cacagcccag       300
cttggagcga acgacctaca ccgaactgag atacctacag cgtgagctat gagaaagcgc       360
ccaatacgca aaccgcctct ccccgcgcgt tggccgattc attatggagc tgttgacaat       420
taatcatcgg ctcgtataat gtgtggaatt gtgagcggat aacaatttca cacaggaaac       480
agaattcaaa ggaggacaac catgcccacc ctcgcgcctt caggtcaact tgaaatccaa       540
gcgatcggtg atgtctccac cgaagccgga gcaatcatta caaacgctga atcgcctat       600 caccgctggg tgaataccg cgtagataaa gaaggacgca gcaatgtcgt tctcatcgaa        660
cacgccctca ctggagattc caacgcagcc gattggtggg ctgacttgct cggtcccggc       720
aaagccatca cactgatat ttactgcgtg atctgtacca acgtcatcgg tggttgcaac        780
ggttccaccg gacctggctc catgcatcca gatggaaatt tctggggtaa tcgcttcccc       840
gccacgtcca ttcgtgatca ggtaaacgcc gaaaaacaat tcctcgacgc actcggcatc       900
accacggtcg ccgcagtact tggtggttcc atgggtggtg cccgcaccct agagtgggcc       960
gcaatgtacc cagaaactgt tggcgcagct gctgttcttg cagtttctgc acgcgccagc      1020
gcctggcaaa tcggcattca atccgcccaa attaaggcga ttgaaaacga ccaccactgg      1080
cacgaaggca actactacga atccggctgc aacccagcca ccggactcgg cgccgcccga      1140
cgcatcgccc acctcacct accgtggcgaa ctagaaatcg acgaacgctt cggcaccaaa      1200
gcccaaaaga acgaaaaccc actcggtccc taccgcaagc ccgaccagcg cttcgccgtg      1260
gaatcctact tggactacca agcagacaag ctagtacagc gtttcgacgc cggctcctac      1320
gtcttgctca ccgacgccct caaccgccac gacattggtc gcgaccgcgg aggcctcaac      1380
```

-continued

| | |
|---|---|
| aaggcactcg aatccatcaa agttccagtc cttgtcgcag gcgtagatac cgatattttg | 1440 |
| taccccctacc accagcaaga acacctctcc agaaacctgg gaaatctact ggcaatggca | 1500 |
| aaaatcgtat cccctgtcgg ccacgatgct ttcctcaccg aaagccgcca atggatcgc | 1560 |
| atcgtgagga acttcttcag cctcatctcc ccagacgaag acaacccttc gacctacatc | 1620 |
| gagttctaca tctaatagac gcgtgagctg ttgacaatta atcatcggct cgtataatgt | 1680 |
| gtggaattgt gagcggataa caatttcacg cgtttaatta acacgagtac tggaaaacta | 1740 |
| aatgccaaag tacgacaatt ccaatgctga ccagtggggc tttgaaaccc gctccattca | 1800 |
| cgcaggccag tcagtagacg cacagaccag cgcacgaaac cttccgatct accaatccac | 1860 |
| cgctttcgtg ttcgactccg ctgagcacgc caagcagcgt ttcgcacttg aggatctagg | 1920 |
| ccctgtttac tcccgcctca ccaacccaac cgttgaggct ttggaaaacc gcatcgcttc | 1980 |
| cctcgaaggt ggcgtccacg ctgtagcgtt ctcctccgga caggccgcaa ccaccaacgc | 2040 |
| cattttgaac ctggcaggag cgggcgacca catcgtcacc tccccacgcc tctacggtgg | 2100 |
| caccgagact ctattcctta tcactcttaa ccgcctgggt atcgatgttt ccttcgtgga | 2160 |
| aaaccccgac gaccctgagt cctggcaggc agccgttcag ccaaacacca aagcattctt | 2220 |
| cggcgagact ttcgccaacc cacaggcaga cgtcctggat attcctgcgg tggctgaagt | 2280 |
| tgcgcaccgc aacagcgttc cactgatcat cgacaacacc atcgctaccg cagcgctcgt | 2340 |
| gcgcccgctc gagctcggcg cagacgttgt cgtcgcttcc ctcaccaagt tctacaccgg | 2400 |
| caacggctcc ggactgggcg gcgtgcttat cgacggcgga agttcgatt ggactgtcga | 2460 |
| aaaggatgga aagccagtat tcccctactt cgtcactcca gatgctgctt accacggatt | 2520 |
| gaagtacgca gaccttggtg caccagcctt cggcctcaag gttcgcgttg gccttctacg | 2580 |
| cgacaccggc tccaccctct ccgcattcaa cgcatgggct gcagtccagg gcatcgacac | 2640 |
| cctttccctg cgcctggagc gccacaacga aaacgccatc aaggttgcag aattcctcaa | 2700 |
| caaccacgag aaggtggaaa aggttaactt cgcaggcctg aaggattccc cttggtacgc | 2760 |
| aaccaaggaa aagcttggcc tgaagtacac cggctccgtt ctcaccttcg agatcaaggg | 2820 |
| cggcaaggat gaggcttggg catttatcga cgccctgaag ctacactcca accttgcaaa | 2880 |
| catcggcgat gttcgctccc tcgttgttca cccagcaacc accacccatt cacagtccga | 2940 |
| cgaagctggc ctggcacgcg cgggcgttac ccagtccacc gtccgcctgt ccgttggcat | 3000 |
| cgagaccatt gatgatatca tcgctgacct cgaaggcggc tttgctgcaa tctagggccg | 3060 |
| gccgtttaaa ccctgcaggt ccgggacctg caggcatgca agcttggcac tggccgtcgt | 3120 |
| tttacaacgt cgtgactggg aaaaccctgg cgttacccaa cttaatcgcc ttgcagcaca | 3180 |
| tccccctttc gccagctggc gtaatagcga agaggcccgc accgatcgcc cttcccaaca | 3240 |
| gttgcgcagc ctgaa | 3255 |